United States Patent
Tinge et al.

(10) Patent No.: US 10,130,895 B2
(45) Date of Patent: Nov. 20, 2018

(54) PROCESS FOR REVAMPING A PLANT FOR THE PRODUCTION OF CYCLOHEXANONE

(71) Applicant: CAP III B.V., Sittard (NL)

(72) Inventors: Johan Thomas Tinge, Sittard (NL); Iris Verschuren, Sittard (NL)

(73) Assignee: CAP III B.V., Urmond (NL)

( * ) Notice: Subject to any disclaimer, the term of this patent is extended or adjusted under 35 U.S.C. 154(b) by 0 days.

(21) Appl. No.: 15/535,795

(22) PCT Filed: Dec. 15, 2015

(86) PCT No.: PCT/EP2015/079774
§ 371 (c)(1),
(2) Date: Jun. 14, 2017

(87) PCT Pub. No.: WO2016/096844
PCT Pub. Date: Jun. 23, 2016

(65) Prior Publication Data
US 2017/0368473 A1    Dec. 28, 2017

(30) Foreign Application Priority Data

Dec. 15, 2014   (EP) ..................... 14197946

(51) Int. Cl.
*B01D 3/00* (2006.01)
*C07C 45/82* (2006.01)
(Continued)

(52) U.S. Cl.
CPC .............. *B01D 3/009* (2013.01); *B01D 3/10* (2013.01); *B01D 3/12* (2013.01); *B01D 3/143* (2013.01);
(Continued)

(58) Field of Classification Search
CPC .. B01D 3/009; B01D 3/10; B01D 3/12; C07C 27/28; C07C 35/08; C07C 35/17;
(Continued)

(56) References Cited

U.S. PATENT DOCUMENTS

| 2,829,166 A | 4/1958 | Joris et al. |
| 5,015,787 A | 5/1991 | Van Peppen |

(Continued)

FOREIGN PATENT DOCUMENTS

| WO | 2009080618 A1 | 7/2009 |
| WO | 2009080621 A1 | 7/2009 |
| WO | 2014001461 A1 | 1/2014 |

OTHER PUBLICATIONS

Dimian, Alexandra C., et al. "Phenol Hydrogenation to Cyclohexanone," Chemical Process Design: Computer-Aided Cases Studies, Mar. 3, 2008, DOI: 10.1002/9783527621583.ch5.
(Continued)

*Primary Examiner* — Renee Robinson
(74) *Attorney, Agent, or Firm* — Honigman Miller Schwartz and Cohn LLP; Fernando Alberdi; Jonathan P. O'Brien

(57) ABSTRACT

A process for the construction of a second chemical plant, which second chemical plant is suitable for the separation of cyclohexanone from a second mixture, which second mixture comprises reaction products from the hydrogenation of phenol. The process comprises providing a first chemical plant, which first chemical plant is suitable for the separation of cyclohexanone from a first mixture, and a second chemical plant comprising a distillation column suitable for distilling overhead cyclohexanone reused from the first chemical plant.

10 Claims, 2 Drawing Sheets

(51) Int. Cl.
*B01D 3/12* (2006.01)
*B01D 3/10* (2006.01)
*B01D 3/14* (2006.01)
*C07C 27/28* (2006.01)
*C07C 35/08* (2006.01)
*C07C 45/00* (2006.01)
*C07C 49/403* (2006.01)

(52) U.S. Cl.
CPC .............. *C07C 27/28* (2013.01); *C07C 35/08* (2013.01); *C07C 45/006* (2013.01); *C07C 45/82* (2013.01); *C07C 49/403* (2013.01); *C07C 2601/14* (2017.05); *Y02P 70/34* (2015.11)

(58) Field of Classification Search
CPC ..... C07C 45/002; C07C 45/006; C07C 45/28; C07C 45/82; C07C 49/403
See application file for complete search history.

(56) References Cited

U.S. PATENT DOCUMENTS

| | | |
|---|---|---|
| 8,618,334 B2 | 12/2013 | Horsels et al. |
| 9,388,107 B2 | 7/2016 | Cap, III |
| 2011/0028675 A1* | 2/2011 | Van Dortmont ........ C07C 29/50 528/165 |
| 2011/0028763 A1 | 2/2011 | Parton et al. |
| 2011/0054142 A1* | 3/2011 | Horsels ................... C07C 29/50 528/129 |
| 2016/0368844 A1 | 12/2016 | Dakka et al. |
| 2017/0233323 A1 | 8/2017 | Becker et al. |

OTHER PUBLICATIONS

International Search Report for PCT/EP2013/063529 dated Sep. 6, 2013.

* cited by examiner

PROCESS FOR REVAMPING A PLANT FOR THE PRODUCTION OF CYCLOHEXANONE

CROSS-REFERENCE TO RELATED APPLICATIONS

This application is a 35 U.S.C. § 371 national phase filing claiming the benefit of and priority to Patent Cooperation Treaty application no. PCT/EP2015/079774, filed Dec. 15, 2015, which claims the benefit of and priority to EP patent application no. 14197946.8, filed on Dec. 15, 2014, the entire contents of the aforementioned disclosures are hereby incorporated by reference herein.

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not Applicable.

STATEMENT REGARDING PRIOR DISCLOSURES BY THE INVENTOR OR A JOINT INVENTOR

Not Applicable.

BACKGROUND OF THE INVENTION

The present invention relates to a process for constructing a chemical plant for the production of cyclohexanone.

Cyclohexanone is an intermediate in the production of, amongst other compounds, adipic acid and caprolactam. These are monomers commonly used in the production of polyamide-6,6 and polyamide-6, respectively. The majority of cyclohexanone for use in producing caprolactam is produced by oxidation of cyclohexane, using atmospheric oxygen. Typically, cyclohexane is produced from hydrogenation of benzene. Oxidation of cyclohexane yields a mixture of cyclohexanol and cyclohexanone and the precursor hydroxyl hydroperoxide which is then thermally and/or catalytically decomposed to produce additional cyclohexanol and cyclohexanone, and a variety of by-products. Cyclohexane constitutes the vast majority of the resulting mixture from the oxidation unit because the conversion rate of the reaction is low. Cyclohexane is removed by distillation and recycled in the process. Cyclohexanone is then separated by distillation from the mixture comprising cyclohexanol, cyclohexanone, unreacted cyclohexane and by-products. Cyclohexanol may also be recovered by distillation and optionally converted to cyclohexanone by dehydrogenation.

One alternative process for the production of cyclohexanone is by the catalytic reduction of phenol with hydrogen, for example using a palladium-comprising catalyst. The reduction of phenol with hydrogen can be performed in the gas phase or in the liquid phase, described in, for example, Michael Tuttle Musser; Cyclohexanol and Cyclohexanone in Ullmann's Encyclopedia of Industrial Chemistry Published Online: 15 Oct. 2011 DOI: 10.1002/14356007.a08_217.pub2 Copyright © 2002 by Wiley-VCH Verlag GmbH & Co. KGaA (Musser); and J. F. Van Peppen, W. B. Fisher and C. H. Chan; 'Phenol Hydrogenation Process' in Chemical Industries, 22 ('Catalysis of Organic Reactions'; Ed. R. L. Augustine); Marcel and Dekker, N.Y., 355-372; (1985)). A mixture comprising cyclohexanol, cyclohexanone, unreacted phenol and by-products is produced. Separation of cyclohexanone from this mixture may be made by distillation. The composition of such a mixture is vastly different to that produced by the oxidation of cyclohexane. Accordingly, the apparatus required for the hydrogenation of phenol is different to that required for the oxidation of cyclohexanone.

Chemical plants for the production of cyclohexanone and cyclohexanol by oxidation of cyclohexane are known in the art, also described in, for example, Musser. Chemical plants have a maximum capacity. A plant may in practice be operated at capacities below this. However, there arises a problem when it is desired to increase the capacity of a chemical plant above the maximum of the current design, for example when increased demand of product is experienced.

One option for expansion is to build a new plant. For example, an existing plant could be substantially copied to provide the increased capacity. A major drawback of this approach is the high cost. Alternatively, the existing plant could be modified by increasing capacity of the rate-limiting components of the plant, a form of "de-bottlenecking". This could be for example by replacing an existing component with another component having a larger capacity, or adding a duplicate component. However, where such rate-limiting components are complex, it may be prohibitively costly to replace or expand them.

BRIEF SUMMARY OF THE INVENTION

The present inventors have discovered a method to significantly increase the capacity of a plant for the production of cyclohexanone. They have developed a process for the construction of a plant to produce cyclohexanone from the hydrogenation of phenol; based on the equipment of a plant used to produce cyclohexanone from the oxidation of cyclohexane. More specifically, the present invention provides a process for the construction of a second chemical plant, which second chemical plant is suitable for the separation of cyclohexanone from a second mixture, which second mixture comprises reaction products from the hydrogenation of phenol, said process comprising:

a) providing a first chemical plant, which first chemical plant is suitable for the separation of cyclohexanone from a first mixture, which first mixture comprises reaction products from the oxidation of cyclohexane, and which first plant comprises:

i) a distillation column suitable for distilling overhead cyclohexane; and ii) a distillation column suitable for distilling overhead cyclohexanone; and b) disabling i) said distillation column suitable for distilling overhead cyclohexane from said first chemical plant.

Typically, in the process of the present invention each of the first chemical plant and the second chemical plant comprise: iii) a distillation column suitable for distilling overhead components having a lower boiling point than cyclohexanone. Preferably, the column in the second chemical plant is the same as that in the first chemical plant. More preferably, the process involves leaving in place the column from the first chemical plant to construct the second chemical plant. When used in the process of separating cyclohexanone, the bottom product of such a column typically comprises a mixture of cyclohexanone, cyclohexanol and by-products.

As used herein leaving in place includes disconnecting and reconnecting the column to the same or different apparatus.

Typically, in the process of the present invention each of the first chemical plant and the second chemical plant comprise: iv) a distillation column suitable for distilling overhead a mixture comprising cyclohexanol and cyclohexanone.

The first chemical plant is suitable for the separation of cyclohexanone from a first mixture, which first mixture comprises reaction products from the oxidation of cyclohexane. The first plant typically includes a cyclohexane oxidation unit for the oxidation of cyclohexane to produce a first mixture of cyclohexanol and cyclohexanone. The cyclohexane oxidation unit for the oxidation of cyclohexane comprises one or more oxidation reactors. In this embodiment, the cyclohexane oxidation unit for the oxidation of cyclohexane is not needed in the second plant. Accordingly, typically, the first chemical plant comprises: v) a cyclohexane oxidation unit suitable for the oxidation of cyclohexane, and the process comprises disabling said cyclohexane oxidation unit.

Further, since the oxidation of cyclohexane is a highly exothermic process, where a cyclohexane oxidation unit for the oxidation of cyclohexane to a mixture of cyclohexanol and cyclohexanone is present, a heat recovery unit for the recovery of heat from off-gas from the oxidation of cyclohexane is typically also employed. In the process of the present invention, the heat recovery will become redundant if the oxidation of cyclohexane becomes redundant. Accordingly, preferably, the first chemical plant comprises: vi) a heat recovery unit suitable for the recovery of heat from off-gas from the cyclohexane oxidation unit suitable for the oxidation of cyclohexane, and the process comprises disabling said heat recovery unit.

More preferably, the first plant further comprises:

iii) a distillation column suitable for distilling overhead components having a lower boiling point that cyclohexanone;

iv) a distillation column suitable for distilling overhead a mixture comprising cyclohexanol and cyclohexanone;

v) a cyclohexane oxidation unit suitable for the oxidation of cyclohexane; and vi) a heat recovery unit suitable for the recovery of heat from off-gas from the cyclohexane oxidation unit suitable for the oxidation of cyclohexane; and wherein the process comprises disabling each of v) said cyclohexane oxidation unit and vi) said heat recovery unit.

"A process for the construction of a second chemical plant from a first chemical plant" is herein defined as a process in which equipment, i.e. at least one apparatus or line, is removed from the first chemical plant and/or in which equipment, i.e. at least one apparatus or line, is added to the first chemical plant in order to provide the second chemical plant. The second chemical plant is the result of retrofitting of the first chemical plant. The first chemical plant does not comprise a phenol hydrogenation unit that produces a mixture comprising reaction products from the hydrogenation of phenol. The second chemical plant preferably comprises a phenol hydrogenation unit that produces a mixture comprising reaction products from the hydrogenation of phenol.

So, typically, the process for the construction of a second chemical plant from a first chemical plant comprises adding a phenol hydrogenation unit to said first chemical plant.

Processes based on oxidation of cyclohexane to produce essentially pure cyclohexanone are known to consume large amounts of energy, typically supplied industrially as steam. Specific steam consumptions of more than 5 tons of steam per ton of purified cyclohexanone are known. Large quantities of steam are consumed in heating cyclohexane fed to the oxidation reactor; the removal of unreacted cyclohexane and the dehydrogenation of cyclohexanol. A further advantage of a process of constructing a plant to carry out a different process according to the present invention is that the energy consumption per unit weight of cyclohexanone produced may be reduced.

Typical carbon efficiency of hydrogenation of phenol to cyclohexanone is higher than 98% and in general even higher than 99%, while the carbon efficiency of oxidation of cyclohexane to cyclohexanone is typically from 75% to 90%. A yet further advantage of constructing a plant according to the present invention is that less starting material is required to produce a certain amount of cyclohexanone. Further, the amount of by-products and therefore waste produced per unit weight of cyclohexanone produced may be reduced. The production of cyclohexanone by the oxidation of cyclohexane is typically subject to stringent safety regulations because of the risk of ignition of explosive cyclohexane-oxygen mixtures. As a result, increasing capacity of a plant may lead to increased safety measures, for example a larger safety circle, needing to be introduced. Yet a further advantage of the process of the present invention is that the risk of explosion of cyclohexane-oxygen mixtures is avoided, because no cyclohexane is used in the process of the constructed plant. Thus the associated safety measures are not required.

The present invention therefore also provides a chemical plant suitable for the separation of cyclohexanone from a second mixture, which second mixture comprises reaction products from the hydrogenation of phenol, which chemical plant comprises:

a) a distillation column suitable for distilling overhead components having a lower boiling point than cyclohexanone;

b) a distillation column suitable for distilling overhead cyclohexanone;

c) a distillation column suitable for distilling overhead a mixture comprising cyclohexanol and cyclohexanone in a wt.:wt. ratio of at least 4:1;

d) a cyclohexanol dehydrogenation unit suitable for the dehydrogenation of cyclohexanol to form a mixture comprising cyclohexanol and cyclohexanone; and e) a feed line suitable for recycling said mixture comprising cyclohexanol and cyclohexanone formed in d) from d) to a);

characterised in that at least one of a) and d) have been used in a chemical plant for the separation of cyclohexanone from a first mixture, which first mixture comprises reaction products from the oxidation of cyclohexane; and wherein at least one of c) and d) has a capacity greater than that necessary for the separation of cyclohexanone from the second mixture, based on the chemical plant operating at full capacity of a) and b).

As used herein a chemical plant is all apparatus necessary to produce cyclohexanone. This includes units for one or multiple chemical or physical operations, for example, distillation, extraction and reaction. It includes all auxiliary equipment, for example reflux units, steam supply, pumps and pipework. The exact apparatus depends on the starting material.

According to the present invention construction of a second chemical plant means modifying a first chemical plant. At least some apparatus of the first chemical plant is present in the second plant. In effect, the second chemical plant replaces the first chemical plant.

The present invention further provides a process for the separation of cyclohexanone from a second mixture, which second mixture comprises reaction products from the hydrogenation of phenol, said process comprising:

a) distilling overhead in a distillation column components having a lower boiling point than cyclohexanone;

b) distilling overhead in a distillation column cyclohexanone;

c) distilling overhead in a distillation column a mixture of cyclohexanol and cyclohexanone in a wt.:wt. ratio of at least 4:1;

d) dehydrogenating in a cyclohexanol dehydrogenation unit cyclohexanol distilled overhead in c) to form a mixture comprising cyclohexanol and cyclohexanone;

e) recycling the mixture comprising cyclohexanol and cyclohexanone formed in d) from d) to a);

characterised in that at least one of the distillation column of a) and the cyclohexanol dehydrogenation unit of d) have been used in a chemical plant for the separation of cyclohexanone from a first mixture, which first mixture comprises reaction products from the oxidation of cyclohexane; and wherein at least one of c) and d) is carried out at a rate below the capacity of, respectively, the distillation column of c) and the cyclohexanol dehydrogenation unit of d).

As used herein, reaction products from the hydrogenation of phenol means compounds resulting from the hydrogenation of phenol. Typically this comprises cyclohexanone, cyclohexanol, at least one characteristic by-product and (unreacted) phenol. The phenol content of the second mixture is typically at least 0.2 wt. %. Preferably it is at least 0.3 wt. %; more preferably at least 0.4 wt. %. The phenol content is preferably less than 50 wt. %; more preferably less than 20 wt. %; most preferably less than 10 wt. %. The cyclohexanone content of the second mixture is typically at least 80 wt. %. Preferably it is at least 85 wt. %; more preferably at least 90 wt. %. The cyclohexanol content is preferably less than 15 wt. %; more preferably less than 10 wt. %; most preferably less than 5 wt. %. Typically, the second mixture comprises at least one characteristic by-product.

Reaction products from the oxidation of cyclohexane means compounds resulting from the oxidation of cyclohexane. Typically, this comprises cyclohexanol, cyclohexanone, at least one characteristic by-product and (unreacted) cyclohexane. The cyclohexane content of the first mixture is typically at least 80 wt. %. Preferably it is at least 85 wt. %; more preferably at least 90 wt. %. The cyclohexanol content is preferably less than 10 wt. %; more preferably less than 7 wt. %; most preferably less than 5 wt. %. The cyclohexanone content of the first mixture is typically less than 10 wt. %. Preferably it is less than 7 wt. %; more preferably less than 5 wt. %. Typically, the second mixture comprises at least one characteristic by-product.

Disabling from said first chemical plant means removing in any way from the process to be carried out by the second chemical plant. This includes disconnecting the distillation column, for example by simply closing the pipework or removing the pipework that connects it to other apparatus of the first chemical plant. It also includes removing the column completely from the first chemical plant.

A dehydrogenation unit is the equipment used to convert cyclohexanol into a mixture comprising cyclohexanol and cyclohexanone. In other words, part of the cyclohexanol is dehydrogenated. Typically a first mixture comprising cyclohexanol and cyclohexanone is fed to the dehydrogenation unit and a second mixture comprising cyclohexanol and cyclohexanone leaves the dehydrogenation unit. The first mixture comprising cyclohexanol and cyclohexanone is typically that produced by distillation overhead. Therefore, it typically has a wt.:wt. ratio of cyclohexanol to cyclohexanone of at least 4:1, preferably at least 5:1, more preferably at least 6:1, and even more preferably at least 10:1. The second mixture comprising cyclohexanol and cyclohexanone has a higher proportion of cyclohexanone than the first mixture comprising cyclohexanol and cyclohexanone. Hydrogen gas is co-produced. In addition several by-products might be formed. The amounts of these by-products are, amongst others, depending on the used type of catalyst, the operating temperature and the age of the catalyst in the dehydrogenation unit. One of these by-products is phenol, which is typically present in an amount from 0 wt. % to less than 0.3 wt. % in the second mixture comprising cyclohexanol and cyclohexanone that leaves the dehydrogenation unit.

The oxidation of cyclohexane can be performed in several ways. Most commonly cyclohexane is oxidized with oxygen from air at pressures ranging from 500 kPa to 2000 kPa and at temperatures ranging from 140° C. to 200° C. to produce cyclohexyl hydroperoxide, which is subsequently decomposed into cyclohexanone and cyclohexanol. Besides these desired components several by-products are formed. The per pass conversion of cyclohexane in a cyclohexane oxidation unit ranges from 2% to 10% in order to limit the formation of by-products. The oxidation of cyclohexane can be performed in the presence of a catalyst or in the absence of a catalyst. The ratio of cyclohexanone to cyclohexanol in the reaction mixture that is obtained after the decomposition of cyclohexyl hydroperoxide is typically from 0.3 to 2. The reaction mixture that is obtained comprises cyclohexanone, cyclohexanol, by-products and (unreacted) cyclohexane and is purified in a multi-step distillation train. Optionally, cyclohexanol is converted into cyclohexanone whereby hydrogen gas is co-produced.

The first mixture typically comprises one or more of the following components: 2-methylcyclohexanone, 3-methylcyclohexanone, 4-methylcyclohexanone, cyclohexylidenecyclohexanone, bicyclohexyl, dicyclohexylether, hexanal, pentanal, 2-heptanone, 3-heptanone, 4-heptanone, 1,3-cyclohexanedione, and 1,4-cyclohexanedione. These are characteristic by-products of the oxidation of cyclohexane. Preferably, the first mixture comprises each of the aforementioned components.

More preferably, the first mixture comprises cyclohexanol, cyclohexanone, cyclohexane and at least one compound selected from hexanal, pentanal, 2-heptanone, 3-heptanone, 4-heptanone, 1,3-cyclohexanedione and 1,4-cyclohexanedione. The phenol content of the first mixture is typically less than 0.4 wt. %. Preferably, it is less than 0.3 wt. %; more preferably less than 0.2 wt. %; most preferably less than 0.1 wt. %.

The reduction of phenol with hydrogen can be performed in the gas phase or in the liquid phase. The hydrogenation catalyst may in principle be any (supported) hydrogenation catalyst capable of catalysing the hydrogenation of phenol. Usually, the catalyst comprises one or more catalytically active metals selected from palladium, platinum, ruthenium, rhodium, iridium, rubidium and osmium. Palladium, platinum or a combination thereof are preferred catalytically active metals.

In general the per pass conversion of phenol in the reaction unit is more than 90%. Optionally, unreacted hydrogen gas and inerts are separated off from the reaction mixture. Usually, unreacted hydrogen gas is re-used in the phenol hydrogenation process.

The second mixture comprising the reaction products is purified in a multi-step distillation train. Recovered phenol may be re-used in the phenol hydrogenation process. Optionally, cyclohexanol may be converted into cyclohexanone whereby hydrogen gas is co-produced. Optionally, co-produced hydrogen is re-used in the phenol hydrogenation process. In addition several by-products might be formed. The amounts of these by-products are, amongst others, depending on the used type of catalyst, the operating temperature and the age of the catalyst in the cyclohexanol dehydrogenation unit.

The second mixture typically comprises one or more of the following components: 2-methylcyclohexanone, 3-methylcyclohexanone, 4-methylcyclohexanone, cyclohexylidenecyclohexanone, benzene, bicyclohexyl, dicyclohexylether, 2-phenylcyclohexanol, 3-phenylcyclohexanol, 4-phenylcyclohexanol, cyclohexylphenylether, benzofuran, 2,3-dimethylbenzofuran, 3-methyl-4-octanone, 4-methyl-3-octanone, 3-methyl-3-octanone, methyl-isopropylcyclohexanol, methyl-isopropylcyclohexanone, and 1-(4-methylpentane-2-yl)-benzene-phenol. These are characteristic by-products of the hydrogenation of phenol. Preferably, the second mixture comprises each of the aforementioned components.

More preferably, the second mixture comprises cyclohexanol, cyclohexanone, phenol and at least one compound selected from 2-phenylcyclohexanol, 3-phenylcyclohexanol, 4-phenylcyclohexanol, cyclohexylphenylether, benzofuran, 2,3-dimethylbenzofuran, 3-methyl-4-octanone, 4-methyl-3-octanone, 3-methyl-3-octanone, methyl-isopropylcyclohexanol, methyl-isopropylcyclohexanone and 1-(4-methylpentane-2-yl)-benzene-phenol.

The first mixture and the second mixture are therefore typically different from each other in at least the following respects: i) the first mixture may comprise one or more of: cyclohexane, hexanal, pentanal, 2-heptanone, 3-heptanone, 4-heptanone, 1,3-cyclohexanedione, and 1,4-cyclohexanedione which are essentially absent from the second mixture; and ii) the second mixture may comprise one or more of: 2-phenylcyclohexanol, 3-phenylcyclohexanol, 4-phenylcyclohexanol, cyclohexylphenylether, benzofuran, 2,3-dimethylbenzofuran, 3-methyl-4-octanone, 4-methyl-3-octanone, 3-methyl-3-octanone, methyl-isopropylcyclohexanol, methyl-isopropylcyclohexanone, and 1-(4-methylpentane-2-yl)-benzene-phenol which are essentially absent from the first mixture.

The ratio of cyclohexanone to cyclohexanol in the first mixture typically differs from the ratio of cyclohexanone to cyclohexanol in the second mixture. The ratio of cyclohexanone to cyclohexanol in the first mixture is in general less than 4, which is very much influenced by the presence, if any, and type and concentration of catalyst in the cyclohexane oxidation unit. Preferably, it is less than 3; more preferably less than 2. The ratio of cyclohexanone to cyclohexanol in a first mixture is in general more than 0.1; more preferably more than 0.2; even more preferably more than 0.3. Preferably, it is from 0.3 to 2. The ratio of cyclohexanone to cyclohexanol in a second mixture is in general more than 4. Typically it is more than 5; preferably it is more than 6; most preferably it is more than 10.

Typically, in the process of the present invention said second chemical plant comprises a distillation column suitable for distilling overhead cyclohexanone, wherein said cyclohexanone is part of a third mixture, which third mixture comprises said second mixture from which components having a lower boiling point than cyclohexanone have been removed. The third mixture typically comprises the second mixture wherein the components having a lower boiling point than cyclohexanone have been removed by distillation overhead. Thus the second chemical plant may comprise: ii) a distillation column suitable for distilling overhead cyclohexanone; and a iii) a distillation column suitable for distilling overhead components having a lower boiling point than cyclohexanone.

Typically, in the process of the present invention each of the first chemical plant and the second chemical plant comprise: iv) a distillation column suitable for distilling overhead a mixture comprising cyclohexanol and cyclohexanone in a wt.:wt. ratio of at least 4:1. Preferably, the distillation column of iv) is suitable for distilling overhead a mixture comprising cyclohexanol and cyclohexanone in a wt.:wt. ratio of at least 5:1. More preferably the wt.:wt. ratio is at least 6:1; yet more preferably at least 10:1. Preferably, the column in the second chemical plant is the same as that in the first chemical plant. More preferably, the process involves leaving in place the column from the first chemical plant to construct the second chemical plant. In the process for separating cyclohexanol, besides a gaseous overhead flow that is discharged from the distillation column also a liquid flow comprising mainly cyclohexanol may optionally be drawn from the distillation column between the feeding point and the top of the distillation column. When used in the process of separating cyclohexanol, the bottom product of such a column comprises by-products with a boiling point higher than cyclohexanol (known as "heavies").

The second chemical plant is suitable for the separation of cyclohexanone from a second mixture comprising reaction products from the hydrogenation of phenol. Phenol has a higher boiling point than each of cyclohexanol and cyclohexanone. Accordingly, it is not preferentially distilled overhead in relation to these components; rather it forms part of the bottom product when distilling overhead cyclohexanol. It is desirable to recover said phenol.

Typically, the process of the present invention comprises adding to the first chemical plant a distillation column suitable for the recovery of phenol from the bottom product of iv) a distillation column suitable for distilling overhead a mixture comprising cyclohexanol and cyclohexanone in a wt.:wt. ratio of at least 4:1. More preferably, the process comprises adding two distillation columns suitable for distilling phenol overhead. Phenol so recovered may be removed as a by-product, or may be recycled to the process. The bottom product of such a column is typically disposed of as waste.

Typically, the process further comprises adding to the first chemical plant a feed line from the distillation column suitable for the recovery of phenol from the bottom product of a distillation column suitable for distilling overhead a mixture comprising cyclohexanol and cyclohexanone in a wt.:wt. ratio of at least 4:1 to a phenol hydrogenation unit for the hydrogenation of phenol. In this way, phenol which is distilled overhead may be recycled to a phenol hydrogenation unit. There, it will be hydrogenated and the reaction products returned to the process. In this way phenol unreacted in a first pass through a phenol hydrogenation unit is ultimately reacted by passing through further times. Further, there is no waste phenol from the process for separating cyclohexanone.

Typically, each of the first chemical plant and the second chemical plant comprise: vii) a cyclohexanol dehydrogenation unit suitable for the dehydrogenation of cyclohexanol to cyclohexanone. Preferably, the cyclohexanol dehydrogenation unit in the second chemical plant is the same as that in the first chemical plant. More preferably, the process involves leaving in place the cyclohexanol dehydrogenation unit from the first chemical plant to construct the second chemical plant.

A typical first chemical plant comprises a cyclohexanol dehydrogenation unit for the dehydrogenation of cyclohexanol to cyclohexanone. This cyclohexanol dehydrogenation unit has typically a relatively large capacity, because the ratio of cyclohexanol to cyclohexanone in the reaction mixture that is obtained after the decomposition of cyclohexyl hydroperoxide is typically from 0.3 to 2. It also has a complex design. A cyclohexanol dehydrogenation reactor operates at relatively high temperatures, typically from 200° C. to 450° C., amongst others depending on type and age of catalyst. Accordingly, a cyclohexanol dehydrogenation unit is difficult to produce and therefore expensive.

A typical second chemical plant according to the present invention comprises a cyclohexanol dehydrogenation unit for the dehydrogenation of cyclohexanol to cyclohexanone. Typically, each of the first chemical plant and the second chemical plant comprise a cyclohexanol dehydrogenation unit for the dehydrogenation of cyclohexanol to cyclohexanone. The mixture comprising cyclohexanol and cyclohexanone produced from hydrogenation of phenol has a significantly higher ratio of cyclohexanone to cyclohexanol, than that of a typical mixture comprising cyclohexanol and cyclohexanone produced from oxidation of cyclohexane. Accordingly, the required capacity of a cyclohexanol dehydrogenation unit for the dehydrogenation of cyclohexanol to cyclohexanone in a second plant is significantly lower than that of a first plant. Nevertheless, the function of the cyclohexanol dehydrogenation unit for the dehydrogenation of cyclohexanol to cyclohexanone in a second plant is the same as that in a first plant. Preferably, the cyclohexanol dehydrogenation unit for the dehydrogenation of cyclohexanol to cyclohexanone of the first chemical plant is the cyclohexanol dehydrogenation unit for the dehydrogenation of cyclohexanol to cyclohexanone of the second chemical plant. This means that for the second plant no replacement cyclohexanol dehydrogenation unit for the dehydrogenation of cyclohexanol to cyclohexanone needs to be designed and installed (a complex and therefore expensive unit).

In the process of oxidation of cyclohexane, low conversion is used, which means that the oxidised mixture comprises mostly (unreacted) cyclohexane. The first step following decomposition to a mixture comprising cyclohexanone and cyclohexanol is typically to remove (and recover) cyclohexane. The cyclohexane is typically distilled overhead and returned to the unit suitable for the oxidation of cyclohexane. In the process of hydrogenation of phenol to produce a mixture comprising cyclohexanol and cyclohexanone, no such excess of cyclohexane is present. Therefore, such a distillation column to distil cyclohexane overhead is unnecessary. Accordingly, in the process according to the present invention, it is typically disabled.

A distillation column suitable for distilling overhead cyclohexane typically produces a bottom product comprising a mixture of cyclohexanone, cyclohexanol and by-products.

By a distillation column suitable for distilling overhead cyclohexanone is meant a distillation column which is suitable for distilling overhead essentially pure cyclohexanone. In the process of separating cyclohexanone according to the present invention, preferably essentially pure cyclohexanone is distilled overhead. The bottom product of such a column comprises a mixture of cyclohexanone, cyclohexanol and by-products.

As used herein, the meaning of "essentially pure" is more than 98 wt. %. Preferably, it is more than 99 wt. %; more preferably more than 99.5 wt. %; even more preferably more than 99.9 wt. %.

A distillation column suitable for distilling overhead cyclohexanone is typically large, and therefore expensive. It must be tall with a large reflux, in order to effectively separate essentially pure cyclohexanone from the relatively impure mixture fed to this column. It must also be wide, resulting from the requirements of processing large volumes of cyclohexanone and of operating the distillation column under relatively low temperatures in order to minimize dimerization of cyclohexanone resulting in high vacuum conditions. A typical chemical plant according to the present invention comprises a column for the distillation of cyclohexanone from a mixture comprising cyclohexanol and cyclohexanone. Typically, the first chemical plant comprises a distillation column for the recovery of cyclohexanone by distillation from a mixture comprising cyclohexanol and cyclohexanone that is produced by oxidation of cyclohexane; and the second chemical plant comprises a distillation column for the recovery of cyclohexanone by distillation from a mixture comprising phenol, cyclohexanol and cyclohexanone that is produced by hydrogenation of phenol.

The distillation column in the chemical plant according to the present invention need not be identical to that of the original plant, for example reflux arrangement may be modified, and connections and superstructure may be adapted. However the basic structure should remain intact.

A preferred plant for the separation of cyclohexanone from a second mixture comprises at least the following units:

a) a distillation column suitable for distilling overhead components having a lower boiling point than cyclohexanone;

b) a distillation column suitable for distilling overhead cyclohexanone;

c) a distillation column suitable for distilling overhead a first mixture comprising cyclohexanol and cyclohexanone in a wt.:wt. ratio of at least 4:1;

d) a cyclohexanol dehydrogenation unit suitable for the dehydrogenation of cyclohexanol to form a second mixture comprising cyclohexanol and cyclohexanone;

e) a feed line suitable for recycling said second mixture comprising cyclohexanol and cyclohexanone formed in d) from d) to a); and either f) or g) or both of f) and g):

f) a distillation column suitable for distilling overhead phenol from the bottom product of step c);

g) a phenol hydrogenation unit suitable for the hydrogenation of phenol to form a mixture comprising cyclohexanol and cyclohexanol.

Preferably, the plant comprises both f) and g) and a feed is present from f) to g).

As mentioned above, one object of the present invention is to improve the capacity of a plant for the separation of cyclohexanone. By capacity is meant the mass of cyclohexanone separated in a given time. Typical units are tonnes per year; commonly expressed as kilotonnes per annum or kta. Typically, the capacity of the second chemical plant for separating cyclohexanone is at least 10% greater than the capacity of the first chemical plant for separating cyclohexanone. Preferably, it is at least 15% greater. More preferably capacity is at least 20% greater. Still more preferably capacity of the second chemical plant is at least 25%, more preferably 30% greater than capacity of the first chemical plant.

In the chemical plant of the present invention, e) the feed line suitable for recycling said mixture comprising cyclohexanone and cyclohexanol formed in d) from d) to a), may pass directly from d) to a); or may pass indirectly from d) to a) through one or more process steps.

In the chemical plant of the present invention, at least one of a) and d) have been used in a chemical plant for the separation of cyclohexanone from a first mixture, which first mixture comprises reaction products from the oxidation of cyclohexane. Preferably, both of a) and d) have been used in a chemical plant for the separation of cyclohexanone from a first mixture, which first mixture comprises reaction products from the oxidation of cyclohexane. Typically, at least one of a) and d) were previously used in a chemical plant for the production of cyclohexanone from cyclohexane. Preferably, both a) and d) were previously used in a chemical plant for the production of cyclohexanone from cyclohexane.

In the process for separation of cyclohexanone of the present invention, e) the feed line suitable for recycling said mixture comprising cyclohexanone and cyclohexanol formed in d) from d) to a), may pass directly from d) to a); or may pass indirectly from d) to a) through one or more process steps.

In the process for separation of cyclohexanone of the present invention, at least one of a) and d) have been used in a chemical plant for the separation of cyclohexanone from a first mixture, which first mixture comprises reaction products from the oxidation of cyclohexane. Preferably, both of a) and d) have been used in a chemical plant for the separation of cyclohexanone from a first mixture, which first mixture comprises reaction products from the oxidation of cyclohexane. Typically, at least one of a) and d) were previously used in a chemical plant for the production of cyclohexanone from cyclohexane. Preferably, both a) and d) were previously used in a chemical plant for the production of cyclohexanone from cyclohexane.

Typically, in the chemical plant suitable for the separation of cyclohexanone according to the present invention, at least one of c) and d) has a capacity of at least 10% greater than that necessary for the separation of cyclohexanone from the second mixture, based on the chemical plant operating at full capacity of a) and b). Preferably both c) and d) are carried out at a rate below the capacity of, respectively, the distillation column of c) and the cyclohexanol dehydrogenation unit of d). Below capacity means preferably below 90% capacity; more preferably below 80% capacity; yet more preferably below 70% capacity; still more preferably below 60% capacity.

Typically, in the process for the separation of cyclohexanone from a second mixture, according to the present invention, at least one of c) and d) is carried out at a rate of at most 90% of the capacity of, respectively, the distillation column of c) and the cyclohexanol dehydrogenation unit of d).

Where the process is carried out at a rate below the capacity of the cyclohexanol dehydrogenation unit of step d), the chemical plant, has an over-capacity in the cyclohexanol dehydrogenation unit. A rate below the capacity of the cyclohexanol dehydrogenation unit of step d) includes that the cyclohexanol dehydrogenation unit is operated either continuously or discontinuously. It is typically operated discontinuously where it is not economical to run the unit continuously at a lower rate than its capacity. Capacity of the cyclohexanol dehydrogenation unit refers to the weight of cyclohexanol that is converted into cyclohexanone in the cyclohexanol dehydrogenation per unit time. Most commonly this is measured in tonnes per annum.

The cyclohexanol dehydrogenation unit comprises a cyclohexanol dehydrogenation reactor. Continuous operation may be at a constant rate or may fluctuate in rate over time. However, the average rate is below the capacity obtainable from the equipment. Continuous operation of a cyclohexanol dehydrogenation reactor below its capacity might also be obtained by sealing off part of the reactor volume, for example, by plugging a fraction of the pipes in case the cyclohexanol dehydrogenation reactor comprises multiple parallel pipes.

Discontinuous operation means any way during normal operation in which the step is not continuously carried out. This includes batch and semi-batch, for example periodic, processes. In one embodiment the mixture of cyclohexanol and cyclohexanone produced overhead in distillation step c) is fed to a buffer tank; while cyclohexanol dehydrogenation step d) is not operating. At a certain moment, for example when the buffer tank becomes substantially full, cyclohexanol dehydrogenation step d) is carried out for a defined period of time, for example until the buffer tank is substantially empty, at which point the cyclohexanol dehydrogenation step d) is stopped. The process is repeated periodically. The advantage of such an arrangement is where the cyclohexanol dehydrogenation step d) may be carried out more efficiently at a higher rate than the output from distillation step c).

In another embodiment of discontinuous operation, the mixture comprising cyclohexanol that is remaining after overhead removal of cyclohexanone in distillation step b) is fed to a buffer tank; while distillation step c) and cyclohexanol dehydrogenation step d) are not operating. At a certain moment, for example when the buffer tank becomes substantially full, the mixture comprising cyclohexanol is passed from the buffer tank to distillation step c), which is carried out for a defined period of time, for example until the buffer tank is substantially empty, at which point distillation step c) is stopped. Cyclohexanol dehydrogenation step d) might be operated at the same time as distillation step c). The process is repeated periodically. The advantage of such an arrangement is where distillation step c) may be carried out more efficiently at a higher rate than the output of the mixture comprising cyclohexanol from distillation step b).

Typically, recycling in step e) is made from step d) to step a) through step 0 further purifying said second mixture. Further purifying may be made to separate unwanted compounds from the mixture of cyclohexanol and cyclohexanone. Hydrogen gas might (partially) be removed from the second mixture of cyclohexanol and cyclohexanone.

Cyclohexane is fed to cyclohexane oxidation unit [A] through line [1]. Cyclohexane oxidation unit [A] comprises one or more oxidation reactors. Air is fed through line [2].

Figure 1:
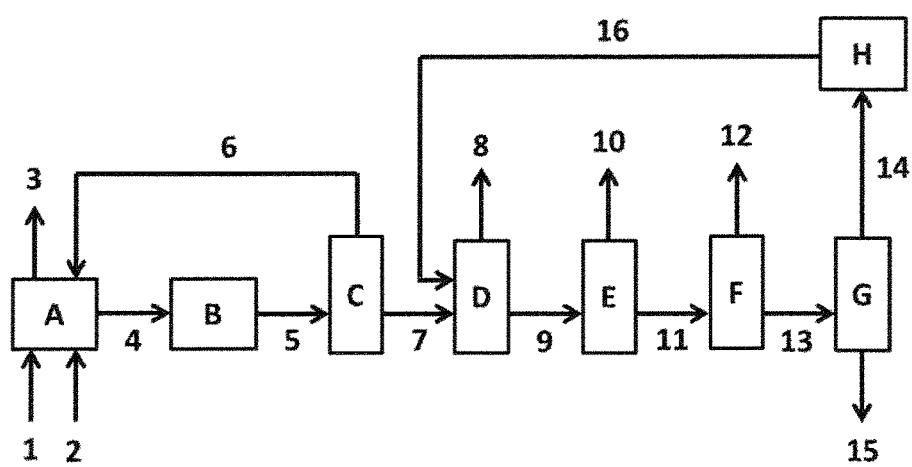
FIG. 1 shows a plant for the production of cyclohexanone by first oxidising cyclohexane and then separating cyclohexanone from the resulting mixture of cyclohexanol and cyclohexanone, and finally dehydrogenating cyclohexanol into a mixture of cyclohexanol and cyclohexanone, i.e. first chemical plant as defined herein.

Off-gases exit through line [3] and are charged to a heat recovery unit (not shown in FIG. 1). The resulting oxidised mixture which comprises cyclohexylhydroperoxide is fed through line [4] to cyclohexylhydroperoxide decomposition unit [B], where cyclohexylhydroperoxide is decomposed into cyclohexanone and/or cyclohexanol. Cyclohexylhydroperoxide decomposition unit [B] comprises one or more cyclohexylhydroperoxide decomposition reactors. Feeding of an aqueous sodium hydroxide solution and a catalyst to, and removal of an aqueous sodium hydroxide solution from, cyclohexylhydroperoxide decomposition unit [B] are not shown in FIG. 1. Decomposed mixture is removed through line [5] to cyclohexane distillation unit [C]. Cyclohexane is distilled overhead in cyclohexane distillation unit [C] and is recycled to cyclohexane oxidation unit [A] through line [6]. Cyclohexane distillation unit [C] comprises one or more cyclohexane distillation columns. The bottom product comprising a mixture of cyclohexanol and cyclohexanone is fed through line [7] to first lights distillation column [D]. Optionally, this bottom product comprising a mixture of cyclohexanol and cyclohexanone is treated with an aqueous sodium hydroxide solution and/or washed with water (not shown in FIG. 1). The optionally treated bottom product is fed to first lights distillation column [D], where a first mixture of components with boiling points below that of cyclohexanone is distilled overhead through line [8]. The bottom product is fed through line [9] to second lights distillation column [E], where a second mixture of components with boiling point below that of cyclohexanone is distilled overhead and removed through line [10]. The bottom product is fed through line [11] to cyclohexanone distillation column [F], where essentially pure cyclohexanone is distilled overhead through line [12]. The bottom product is fed through line [13] to cyclohexanol distillation column [G], where a mixture comprising cyclohexanol and cyclohexanone is distilled overhead. The bottom product is removed through line [15]. The mixture comprising cyclohexanol and cyclohexanone is passed through line [14] to cyclohexanol dehydrogenation unit [H]. Cyclohexanol dehydrogenation unit [H] comprises one or more cyclohexanol dehydrogenation reactors. The resulting dehydrogenated mixture comprising cyclohexanone is, after separating of hydrogen gas (not shown in FIG. 1), recycled through line [16] to the first lights distillation column [D]. Optionally, the resulting dehydrogenated mixture comprising cyclohexanone is, after separating of hydrogen gas (not shown in FIG. 1), recycled through line [16] to second lights distillation column [E] (not shown in FIG. 1).

Figure 2:
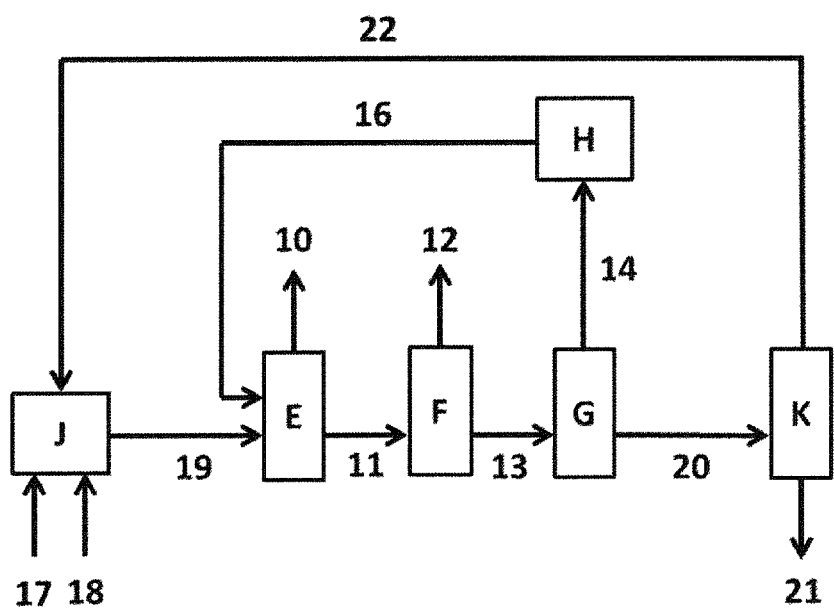

FIG. 2 shows a plant according to the present invention, for the production of cyclohexanone by first hydrogenating phenol, then separating cyclohexanone from the resulting mixture comprising cyclohexanol and cyclohexanone and finally dehydrogenating cyclohexanol into cyclohexanone.

Phenol is fed via line [17], and hydrogen gas is fed through line [18] to a phenol hydrogenation unit [J]. Phenol hydrogenation unit [J] comprises one or more phenol hydrogenation reactors. The resulting mixture of reaction products, comprising phenol, cyclohexanol and cyclohexanone is fed through line [19] to lights distillation column [E]. Optionally, unreacted hydrogen gas and inert gases are separated from this mixture (not shown in FIG. 2). A mixture of components with boiling points below that of cyclohexanone is distilled overhead and removed through line [10]. The bottom product is fed through line [11] to cyclohexanone distillation column [F], where cyclohexanone is distilled overhead through line [12]. The bottom product is fed through line [13] to cyclohexanol distillation column [G], where a mixture comprising cyclohexanol and cyclohexanone is distilled overhead and passed through line [14] to cyclohexanol dehydrogenation unit [H]. Cyclohexanol dehydrogenation unit [H] comprises one or more cyclohexanol dehydrogenation reactors. The resulting mixture comprising cyclohexanone is, after separating of hydrogen gas (not shown in FIG. 2), recycled through line [16] to lights distillation column [E]. Optionally, this hydrogen gas is charged to phenol hydrogenation unit [J] (not shown in FIG. 2). The bottom product of [G] comprising phenol is removed through line [20]. Line [20] leads to phenol distillation column [K] where a mixture comprising phenol is distilled overhead and fed through line [22] to phenol hydrogenation unit [J]. The bottom product is removed from phenol distillation column [K] through line [21]. Optionally, storage tanks are present to store the bottom product of cyclohexanone distillation column [F] that is fed through line [13] and/or to store the mixture comprising cyclohexanol and cyclohexanone that is passed through line [14] to cyclohexanol dehydrogenation unit [H] and/or to store the mixture comprising cyclohexanol and cyclohexanone that is passed through line [16] to lights distillation column [E].

According to one embodiment of the present invention, a chemical plant according to FIG. 2 is constructed from a chemical plant according to FIG. 1. From a comparison of FIG. 2 with FIG. 1, it can be seen that the following apparatus is removed from the first chemical plant (FIG. 1) when constructing the second chemical plant (FIG. 2): cyclohexane oxidation unit [A] together with input lines [1] and [2] and output lines [3] and [4]; decomposition unit [B] together with output line [5]; cyclohexane distillation unit [C] together with output lines [6] and [7]; and first lights distillation column [D] together with output lines [8] and [9]. Further, the following equipment is added to the first chemical plant (FIG. 1) when constructing the second chemical plant (FIG. 2): phenol hydrogenation unit [J] together with input lines [17] and [18] and output line [19]; and phenol distillation column [K] together with feed [20] from cyclohexanol distillation column [G], output [21] and output [22]. Line [16] is relocated from feeding [D] to feeding [E].

The present invention is illustrated by, but not intended to be limited to, the following examples.

DETAILED DESCRIPTION OF THE INVENTION

Comparative Experiment A

A chemical plant for the production of cyclohexanone by oxidation of cyclohexane, comprising:
a cyclohexane oxidation unit;
a heat recovery unit;
a cyclohexylhydroperoxide decomposition unit;
a cyclohexane recovery unit;
a first lights distillation column;
a second lights distillation column;
a cyclohexanone distillation column;
a cyclohexanol distillation column; and
a cyclohexanol dehydrogenation unit;
as described above and substantially as depicted in FIG. 1, was simulated in Aspen Plus® chemical engineering software with input data obtained from an operating chemical plant as described herein. The simulated plant was designed with an hourly capacity of 12.5 metric tons of essentially pure cyclohexanone, which is equivalent to an annual plant capacity of approximately 100 kta of essentially pure cyclohexanone (assuming 8000 effective production hours per year).

The oxidation of cyclohexanone in the cyclohexane oxidation unit was performed without addition of any catalyst. The reaction mixture exiting the cyclohexane oxidation unit was cooled down and was fed to the cyclohexylhydroperoxide decomposition unit. In the cyclohexylhydroperoxide decomposition unit cyclohexylhydroperoxide was decomposed in the presence of an aqueous sodium hydroxide solution and in the presence of dissolved cobalt-salts as catalyst.

The cyclohexane recovery unit comprised three cyclohexane distillation columns that were operated in-series. In the cyclohexane recovery unit cyclohexane was removed by distillation overhead from the decomposed reaction mixture and was recycled to the cyclohexane oxidation unit. The resulting mixture that mainly comprised cyclohexanol and cyclohexanone was washed with water and fed to the first lights distillation column. In the first lights distillation column amongst others water and cyclohexane were distilled overhead. The bottom flow of the first lights distillation column was fed to the second lights distillation column, where components having a boiling point lower than that of cyclohexanone, including cyclohexene epoxide, were distilled overhead. The bottom flow of the second lights distillation column was fed to the cyclohexanone distillation column, where essentially pure cyclohexanone was distilled overhead. The bottom flow of the cyclohexanone distillation column was fed to the cyclohexanol distillation column, where heavies were separated from a mixture comprising mainly cyclohexanol. In the cyclohexanol dehydrogenation unit the mixture comprising mainly cyclohexanol was partially converted into cyclohexanone. The produced reaction mixture was, after separation of formed hydrogen gas, fed to the first lights distillation column.

The cyclohexanone distillation column was a vacuum distillation column with a diameter of 3.3 m, containing 3 beds, each of which have a height of 7.5 m of Mellapak 250Y packing, of which 2 beds were located above the feed inlet. The fractional capacity of the packing (Mellapak 250Y) was approximately 0.88, defined according to the generalized pressure drop correlation of the Eckert method, as illustrated in FIG. 9-21C Ernest E. Ludwig, Applied Process Design for Chemical and Petrochemical Plants, Volume 2, 3rd edition, 1997, p. 283.

The column was equipped with a condenser unit and a steam driven reboiler. Reflux was fed above the top bed. The pressure at the top of the column was approximately 5 kPa. The vapour leaving the top of this column was liquefied in a condenser unit with a maximum duty of about 18 GJ/hr. Part of the obtained liquid was fed to the top of this column as reflux, and the other part was discharged as essentially pure cyclohexanone. The required energy for the distillation process in the cyclohexanone distillation column was introduced by means of indirect heating via steam in a reboiler with a maximum duty of about 18 GJ/hr. The cyclohexanol concentration in the essentially pure cyclohexanone that was distilled overhead in the cyclohexanone distillation column was on average about 250 ppm by weight.

The maximum feed rate to the cyclohexanone distillation column was about 21.8 ton/hr. The weight ratio of cyclohexanone to cyclohexanol in the feed was about 1.4. The reflux rate was about 29.8 ton/hr. The bottom flow rate of the cyclohexanone distillation column was about 9.3 ton/hr and consisted of mainly cyclohexanol and about 6% by weight of cyclohexanone. The feed rate to the cyclohexanol dehydrogenation unit was about 9 ton/hr. The weight ratio of cyclohexanone to cyclohexanol in the outlet of the cyclohexanol dehydrogenation unit was about 6 to 4.

Comparative Experiment B

The process for the production of cyclohexanone was identical to that of Comparative Example A, with the following exceptions:
i) the oxidation of cyclohexanone in the cyclohexane oxidation unit was performed with addition of cobalt-salts as catalyst; and
ii) the mixture resulting from the cyclohexane recovery unit that mainly comprised cyclohexanol and cyclohexanone was after being treated with an aqueous sodium hydroxide solution to saponify esters then washed with water and fed to the first lights distillation column.

In this plant the cyclohexanone distillation column, including all auxiliaries including reboiler and condenser unit was the same as the cyclohexanone distillation column, with all auxiliaries including reboiler and condenser unit, as used in Comparative Experiment A. The pressure at the top of the cyclohexanone distillation column was identical to the pressure in Comparative Experiment A. The cyclohexanol concentration in the essentially pure cyclohexanone that was distilled overhead in the cyclohexanone distillation column was on average about 250 ppm by weight, which is equal to that in Comparative Experiment A. This cyclohexanone distillation column was operated at full load. All other parts of the plant were not limiting the capacity of the plant.

The feed rate to the cyclohexanone distillation column was about 25.9 ton/hr. The weight ratio of cyclohexanone to cyclohexanol in the feed was about 1.0. The reflux rate was about 30.2 ton/hr. The bottom flow rate of the cyclohexanone distillation column was about 13.9 ton/hr and consisted mainly of cyclohexanol and about 6% by weight of cyclohexanone. The feed rate to the cyclohexanol dehydrogenation unit was about 13.3 ton/hr. The weight ratio of cyclohexanone to cyclohexanol in the outlet of the cyclohexanol dehydrogenation unit was about 6 to 4.

The hourly capacity of the cyclohexanone distillation column was about 12.0 metric tons of essentially pure cyclohexanone, which is equivalent to an annual plant capacity of approximately 96 kta of essentially pure cyclohexanone (assuming 8000 effective production hours per year).

In Examples 1 and 2 (according to the invention), the cyclohexanone distillation columns, with all auxiliaries including reboilers and condenser units, were the same as the cyclohexanone distillation columns, including all auxiliaries like reboilers and condenser units, in Comparative Experiments A and B.

Example 1

A chemical plant for the production of cyclohexanone by hydrogenation of phenol, comprising:
a phenol hydrogenation unit;
a lights distillation column;
a cyclohexanone distillation column;
a cyclohexanol distillation column;
a phenol distillation column; and a cyclohexanol dehydrogenation unit;
as described before and substantially as depicted in FIG. 2 was simulated in Aspen Plus® chemical engineering software with input data obtained from an operating chemical plant as described herein. The simulated plant was designed with an identical cyclohexanone distillation column and an identical cyclohexanol dehydrogenation unit as in Comparative Example A. The cyclohexanone distillation column limited the overall capacity of the plant.

The hydrogenation of phenol in the phenol hydrogenation unit was performed in the gas phase in the presence of a palladium-comprising catalyst. The resulting gas mixture, comprising phenol, hydrogen gas, cyclohexanol and cyclohexanone, was partially condensed by cooling and separated into a liquid mixture comprising phenol, cyclohexanol and cyclohexanone that was fed to the lights distillation column, and a gaseous flow comprising hydrogen.

In the lights distillation column, components with boiling points lower than that of cyclohexanone were distilled overhead. The bottom flow from the lights distillation column was fed to the cyclohexanone distillation column, where essentially pure cyclohexanone was distilled overhead. The bottom flow from the cyclohexanone distillation column was fed to the cyclohexanol distillation column, where a mixture comprising mainly cyclohexanol was distilled overhead. This mixture comprising mainly cyclohexanol was fed to the cyclohexanol dehydrogenation unit, in which cyclohexanol was converted into cyclohexanone. Hydrogen gas formed was separated therefrom. The resulting reaction mixture was then fed to the lights distillation column.

The bottom flow of the cyclohexanol distillation column was fed to a phenol distillation column where heavies were separated from a mixture comprising mainly cyclohexanol and phenol.

The pressure at the top of the cyclohexanone distillation column was identical to the pressure in Comparative Experiment A. The cyclohexanol concentration in the cyclohexanone that was distilled overhead in the cyclohexanone distillation column was on average about 250 ppm by weight, which is equal to that in Comparative Experiment A.

The cyclohexanol dehydrogenation unit was identical to the cyclohexanol dehydrogenation unit in Comparative Experiment A.

The feed rate to the cyclohexanone distillation column was about 16.9 ton/hr. The weight ratio of cyclohexanone to cyclohexanol in the feed was almost 11. The reflux rate is about 27.2 ton/hr. The hourly capacity of this column was about 15.0 metric tons of essentially pure cyclohexanone, which is equivalent to an annual plant capacity of approximately 120 kta of essentially pure cyclohexanone.

The flow rate from the bottom of the cyclohexanone distillation column was about 1.9 ton/hr and the flow consisted of mainly cyclohexanol and phenol, and about 6% by weight of cyclohexanone. This bottom flow was fed to the cyclohexanol distillation column where mainly cyclohexanol was distilled overhead. The top flow of this cyclohexanol distillation column was fed to a cyclohexanol dehydrogenation unit. The weight ratio of cyclohexanone to cyclohexanol in the outlet of the cyclohexanol dehydrogenation unit was about 6 to 4. The outlet flow of the cyclohexanol dehydrogenation unit was, after hydrogen gas had been separated off, fed to the lights distillation column. The cyclohexanol dehydrogenation unit was operated at approximately 15% of its capacity.

Comparison of Comparative Experiment A and Example 1 shows that the vacuum distillation column where essentially pure cyclohexanone was distilled overhead (with auxiliaries including reboiler and condenser unit) used in the production of cyclohexanone from reaction products of the oxidation of cyclohexane, can be re-used for the production of cyclohexanone from reaction products of the hydrogenation of phenol. The annual capacity is increased from approximately 100 kta of essentially pure cyclohexanone to approximately 120 kta of essentially pure cyclohexanone, so by about 20%.

In addition, this comparison shows that a cyclohexanol dehydrogenation unit used in a process for the production of cyclohexanone by oxidation of cyclohexane whereby the oxidation of cyclohexane is performed without addition of any catalyst, can be re-used in a process for the production of cyclohexanone by hydrogenation of phenol. In this case, the simulation showed that the cyclohexanol dehydrogenation unit had a huge over-capacity. In practice the capacity of the cyclohexanol dehydrogenation unit could be easily reduced by, for example, blinding off a large fraction of the pipes in case the cyclohexanol dehydrogenation unit comprises a multi-tubular heated reactor.

Example 2

A chemical plant for the production of cyclohexanone by hydrogenation of phenol, comprising:
  a phenol hydrogenation unit;
  a lights distillation column;
  a cyclohexanone distillation column;
  a cyclohexanol distillation column;
  a phenol distillation column; and
  a cyclohexanol dehydrogenation unit;
  as described before and substantially as depicted in FIG. 2 was simulated in Aspen Plus® chemical engineering software with input data obtained from an operating chemical plant as described herein. The simulated plant was designed with an identical cyclohexanone distillation column and an identical cyclohexanol dehydrogenation unit as in Comparative Example B. The cyclohexanone distillation column limited the overall capacity of the plant.

The cyclohexanone plant simulated was identical to that of Example 1, except that it included an additional buffer vessel upstream and an additional buffer vessel downstream of the cyclohexanol dehydrogenation unit.

The process was also identical to that of Example 1, except that:
  i) the hydrogenation of phenol in the phenol hydrogenation unit was performed in the liquid phase with a palladium-comprising catalyst; and
  ii) the resulting reaction mixture that comprised phenol, cyclohexanol and cyclohexanone had a similar composition to that of Example 1.

The top flow of the cyclohexanol distillation column was fed to the buffer tank located upstream of the cyclohexanol dehydrogenation unit. The cyclohexanol dehydrogenation unit was fed from this buffer tank. The cyclohexanol dehydrogenation unit was only operated in a discontinuous manner. It was started when the buffer tank located upstream of the cyclohexanol dehydrogenation unit became about 80% full and was stopped when this tank became less than about 15% full. The weight ratio of cyclohexanone to cyclohexanol in the outlet of the cyclohexanol dehydrogenation unit is about 6 to 4. The outlet flow of the cyclohexanol dehydrogenation unit was, after hydrogen gas had been separated off, fed to the buffer tank located downstream of the cyclohexanol dehydrogenation unit. From this tank a mixture comprising cyclohexanol and cyclohexanone was fed to the lights distillation column in a continuous manner.

The hourly capacity of the cyclohexanone plant was about 15.0 metric tons of essentially pure cyclohexanone, which is equivalent to an annual plant capacity of approximately 120 kta of essentially pure cyclohexanone.

Comparison of Comparative Experiment B and Example 2 shows that the vacuum distillation column where essentially pure cyclohexanone is distilled overhead (with auxiliaries including reboiler and condenser unit) used in the production of cyclohexanone from reaction products of the oxidation of cyclohexane, can be re-used for the production of cyclohexanone from reaction products of the hydrogenation of phenol. The annual capacity is increased from approximately 96 kta of essentially pure cyclohexanone to approximately 120 kta of essentially pure cyclohexanone, so by about 25%.

In addition this comparison shows that the cyclohexanol dehydrogenation unit used in a process for the production of cyclohexanone by oxidation of cyclohexane whereby the oxidation of cyclohexane is performed with addition of catalyst, can be re-used in a process for the production of cyclohexanone by hydrogenation of phenol by operating the cyclohexanol dehydrogenation unit in a discontinuous mode after addition of just two simple buffer tanks.

The invention claimed is:

1. A process for the construction of a second chemical plant, which second chemical plant is suitable for the separation of cyclohexanone from a second mixture, which second mixture comprises reaction products from the hydrogenation of phenol, said process comprising:
   a) providing a first chemical plant, which first chemical plant is suitable for the separation of cyclohexanone from a first mixture, which first mixture comprises reaction products from the oxidation of cyclohexane, and which first plant comprises:
      i) a distillation column suitable for distilling overhead cyclohexane;
      ii) a distillation column suitable for distilling overhead components having a lower boiling point than cyclohexanone;
      iii) a distillation column suitable for distilling overhead cyclohexanone;
      iv) a distillation column suitable for distilling overhead a mixture comprising cyclohexanol and cyclohexanone;
      v) a cyclohexane oxidation unit suitable for the oxidation of cyclohexane; and
      vi) a heat recovery unit suitable for the recovery of heat from off-gas from the cyclohexane oxidation unit suitable for the oxidation of cyclohexane;
   b) disabling i) said distillation column suitable for distilling overhead cyclohexane from said first chemical plant, v) said cyclohexane oxidation unit and vi) said heat recovery unit, and wherein said second chemical plant comprises said distillation column suitable for distilling overhead cyclohexanone, wherein said cyclohexanone is part of a third mixture, which third mixture comprises said second mixture from which components having a lower boiling point than cyclohexanone have been removed; and
   c) adding to said first chemical plant a phenol hydrogenation unit.

2. The process according to claim 1, wherein the first mixture comprises cyclohexanol, cyclohexanone, cyclohexane and at least one compound selected from hexanal, pentanal, 2-heptanone, 3-heptanone, 4-heptanone, 1,3-cyclohexanedione and 1,4-cyclohexanedione.

3. The process according to claim 1, wherein the second mixture comprises cyclohexanol, cyclohexanone, phenol and at least one compound selected from 2-phenylcyclohexanol, 3-phenylcyclohexanol, 4-phenylcyclohexanol, cyclohexylphenylether, benzofuran, 2,3-dimethylbenzofuran, 3-methyl-4-octanone, 4-methyl-3-octanone, 3-methyl-3-octanone, methyl-isopropylcyclohexanol, methyl-isopropylcyclohexanone and 1-(4-methylpentane-2-yl)-benzene-phenol.

4. The process according to claim 1, wherein iv) is suitable for distilling overhead a mixture comprising cyclohexanol and cyclohexanone in a wt.:wt. ratio of at least 4:1.

5. The process according to claim 1, comprising adding to the first chemical plant a distillation column suitable for the recovery of phenol from the bottom product of a distillation column suitable for distilling overhead a mixture comprising cyclohexanol and cyclohexanone in a wt.:wt. ratio of at least 4:1.

6. The process according to claim 5, comprising adding to the first chemical plant a feed line from the distillation column suitable for the recovery of phenol from the bottom product of said distillation column suitable for distilling overhead a mixture comprising cyclohexanol and cyclohexanone in a wt.:wt. ratio of at least 4:1 to said phenol hydrogenation unit.

7. The process according to claim 6, wherein each of the first chemical plant and second chemical plant comprises:
   vii) a cyclohexanol dehydrogenation unit suitable for the dehydrogenation of cyclohexanol to cyclohexanone.

8. The process according to claim 1, wherein the capacity of the second chemical plant for separating cyclohexanone is at least 10% greater than the capacity of the first chemical plant for separating cyclohexanone, wherein capacity means the mass of cyclohexanone separated in a given time.

9. A process for the separation of cyclohexanone from a second mixture, which second mixture comprises reaction products from the hydrogenation of phenol, said process comprising:
   a) distilling overhead in a distillation column components having a lower boiling point than cyclohexanone;
   b) distilling overhead in a distillation column cyclohexanone;
   c) distilling overhead in a distillation column a mixture of cyclohexanol and cyclohexanone in a wt.:wt. ratio of at least 4:1;
   d) dehydrogenating in a cyclohexanol dehydrogenation unit cyclohexanol distilled overhead in c) to form a mixture comprising cyclohexanol and cyclohexanone;
   e) recycling the mixture comprising cyclohexanol and cyclohexanone formed in d) from d) to a); and
   f) hydrogenating phenol in a phenol hydrogenation until that produces a mixture comprising reaction products from the hydrogenation of phenol;
characterised in that at least one of the distillation column of a) and the cyclohexanol dehydrogenation unit of d) have been used in a chemical plant for the separation of cyclohexanone from a first mixture, which first mixture comprises reaction products from the oxidation of cyclohexane; and wherein at least one of c) and d) is carried out at a rate below the capacity of, respectively, the distillation column of c) and the cyclohexanol dehydrogenation unit of d), wherein capacity of the plant or distillation column means the mass of cyclohexanone separated in a given time, and wherein capacity of the cyclohexanol dehydrogenation unit means the weight of cyclohexanol that is converted into cyclohexanone unit per unit time.

10. The process according to claim 9, wherein at least one of c) and d) is carried out at a rate of at most 90% of the capacity of, respectively, the distillation column of c) and the cyclohexanol dehydrogenation unit of d).

* * * * *